(12) United States Patent
Bianco et al.

(10) Patent No.: US 8,633,347 B2
(45) Date of Patent: Jan. 21, 2014

(54) ABSORBING ELEMENT FOR SANITARY PRODUCTS, HAVING EXPANDABLE POCKETS CONTAINING SUPERABSORBENT MATERIAL AND MANUFACTURING PROCESS

(75) Inventors: Carlo Bianco, Pescara (IT); Domenico Polidori, Pescara (IT); Tonino De Angelis, Pescara (IT)

(73) Assignee: Fameccanica.Data S.p.A., Sambuceto di San Giovanni Teatino (IT)

( * ) Notice: Subject to any disclaimer, the term of this patent is extended or adjusted under 35 U.S.C. 154(b) by 567 days.

(21) Appl. No.: 12/593,109

(22) PCT Filed: Dec. 3, 2007

(86) PCT No.: PCT/IB2007/003904
§ 371 (c)(1),
(2), (4) Date: Sep. 25, 2009

(87) PCT Pub. No.: WO2008/117109
PCT Pub. Date: Oct. 2, 2008

(65) Prior Publication Data
US 2010/0100065 A1    Apr. 22, 2010

(30) Foreign Application Priority Data
Mar. 26, 2007    (EP) .................................... 07425178

(51) Int. Cl.
*A61F 13/15*    (2006.01)
(52) U.S. Cl.
USPC ........... 604/378; 604/380; 604/382; 604/383; 604/385.01; 156/276
(58) Field of Classification Search
USPC .................... 604/378, 380, 382, 383, 385.01; 156/276
See application file for complete search history.

(56) References Cited

U.S. PATENT DOCUMENTS

| 4,381,783 A | 5/1983 | Elias |
| 4,578,078 A | 3/1986 | Arkell |

(Continued)

FOREIGN PATENT DOCUMENTS

| EP | 0 875 224 | 11/1998 |
| EP | 1 621 166 | 1/2006 |

(Continued)

OTHER PUBLICATIONS

Japanese Patent Office Action dated Jun. 5, 2012, from Japanese Patent Application No. 2010-500372, and its English translation.

(Continued)

*Primary Examiner* — Jacqueline F. Stephens
(74) *Attorney, Agent, or Firm* — Nixon & Vanderhye P.C.

(57) ABSTRACT

An absorbent element for the absorption of body fluids in sanitary articles comprises a first layer of sheet material presenting an array of hollowed formations (16) with respective mouth parts, as well as masses (18) of superabsorbent material that is able to expand as a result of the absorption of body fluid, which are set in the aforesaid hollowed formations (16). A second layer of sheet material (12) is applied on the first layer of sheet material (10) so as to cover the mouth parts of the hollowed formations (16). At least one of the layers of sheet material (10, 12) is permeable to body fluids to enable the body fluids themselves to penetrate into the hollowed formations and be absorbed by the masses of superabsorbent material (18) that expand in the hollowed formations (16), creating a first level of absorption of body fluids. The second layer of sheet material (12) is compliant in an area corresponding to the mouth parts of the hollowed formations (16) and enables further expansion of said masses of superabsorbent material (18) beyond said hollowed formations (16) so as to create a second level of absorption of body fluids. The first layer (10) and the second layer (12) of sheet material are connected to one another by adhesive formations (14c) that leave the mouth parts of the hollowed formations (16) at least partially free.

48 Claims, 5 Drawing Sheets

(56) References Cited

U.S. PATENT DOCUMENTS

| | | | |
|---|---|---|---|
| 4,600,458 | A | 7/1986 | Kramer et al. |
| 4,681,577 | A | 7/1987 | Stern et al. |
| 4,685,914 | A | 8/1987 | Holtman |
| 4,892,535 | A | 1/1990 | Björnberg et al. |
| 5,505,720 | A * | 4/1996 | Walters et al. ............ 604/378 |
| 5,643,238 | A | 7/1997 | Baker |
| 5,788,684 | A | 8/1998 | Abuto et al. |
| 5,863,288 | A | 1/1999 | Baker |
| 5,938,650 | A | 8/1999 | Baer |
| 6,068,620 | A | 5/2000 | Chmielewski |
| 6,129,717 | A | 10/2000 | Fujioka et al. |
| 6,832,905 | B2 | 12/2004 | Delzer et al. |
| 2003/0208174 | A1 | 11/2003 | Minato et al. |
| 2005/0003191 | A1 | 1/2005 | Ehrnsperger et al. |

FOREIGN PATENT DOCUMENTS

| | | |
|---|---|---|
| JP | 10-510743 | 10/1998 |
| JP | 2004-121390 | 4/2004 |
| JP | 2004-174234 | 6/2004 |
| JP | 2007-14801 | 1/2007 |
| WO | WO 96/19173 A1 | 6/1996 |
| WO | WO 2005/004939 | 1/2005 |
| WO | WO 2006/015138 A1 | 2/2006 |

OTHER PUBLICATIONS

Written Opinion of the International Searching Authority for PCT/IB2007/003904, mailed Jun. 30, 2008.

* cited by examiner

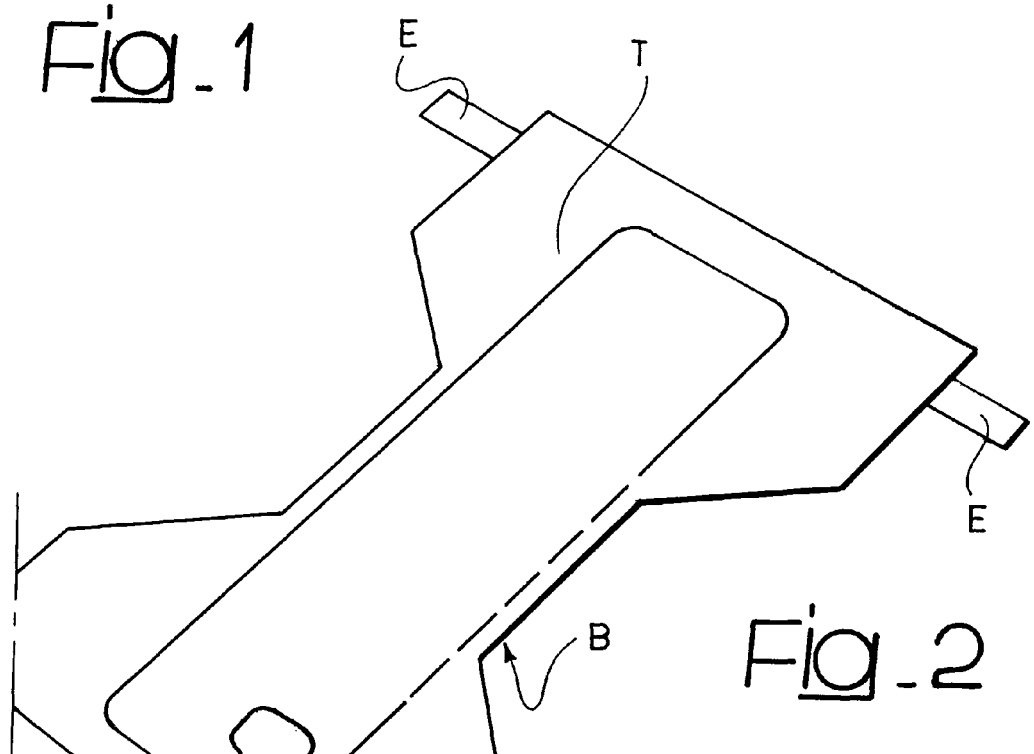
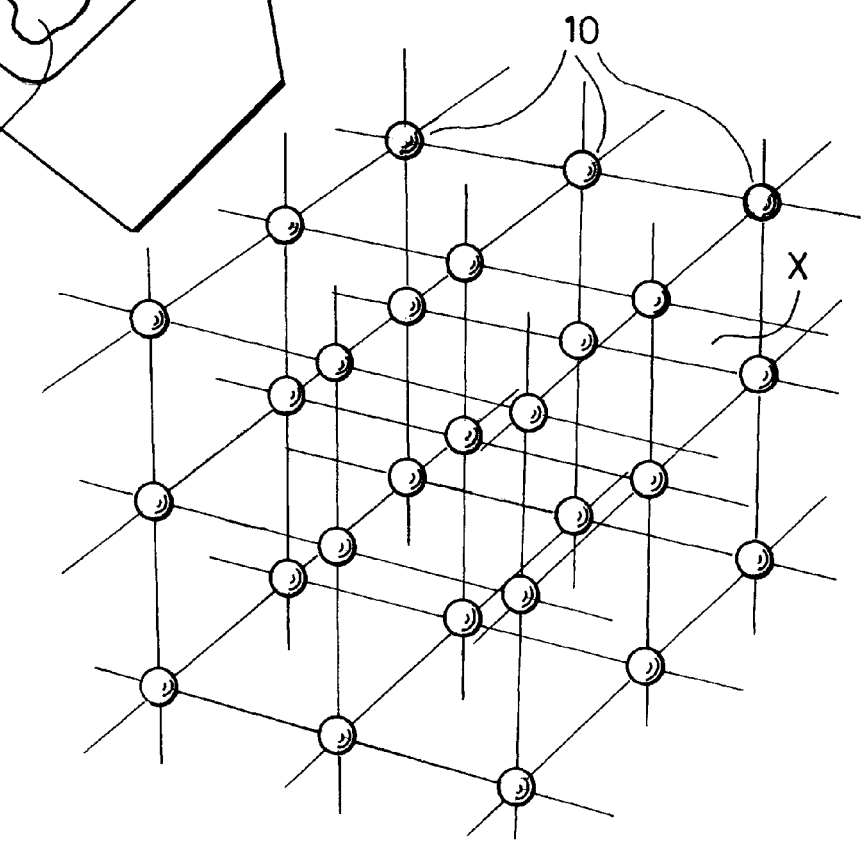

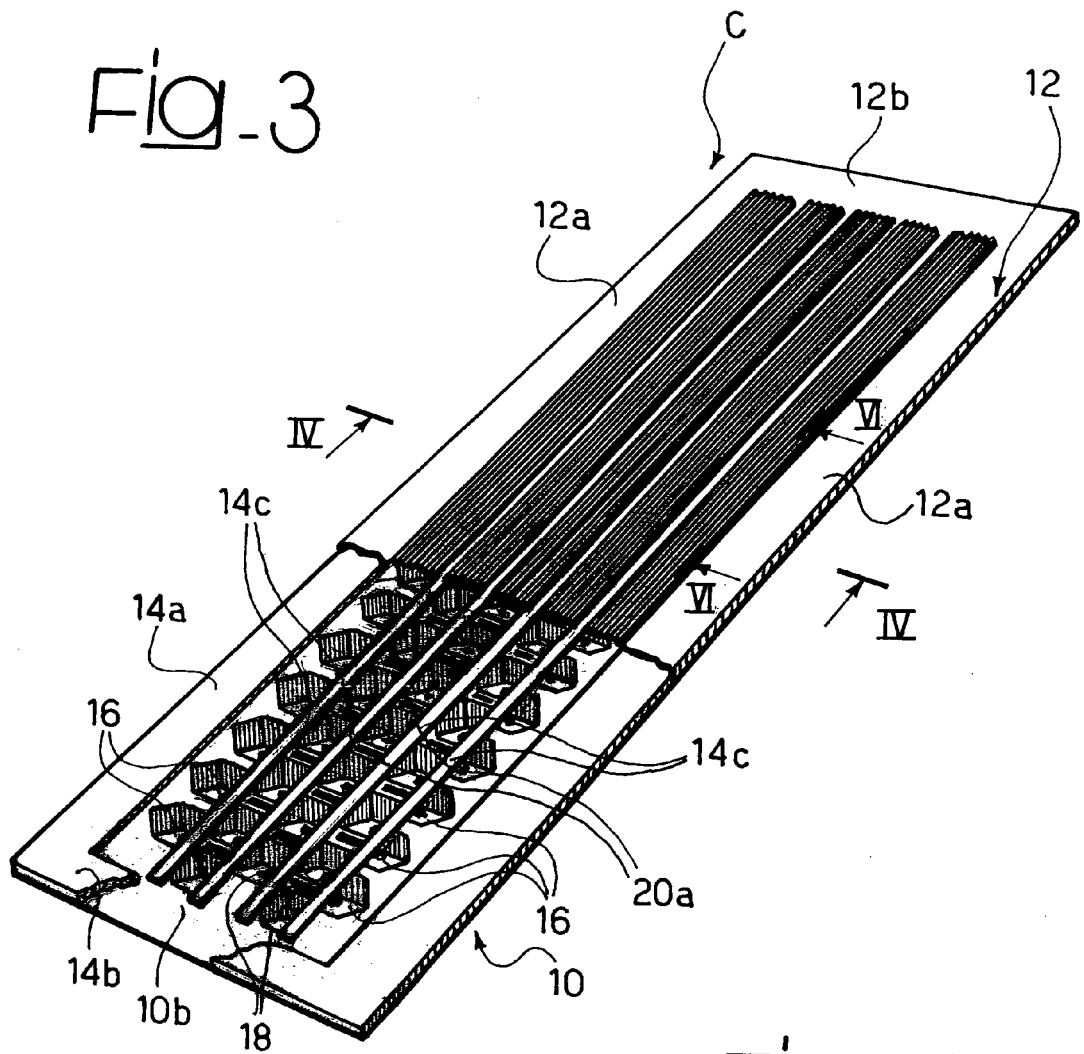
Fig_3
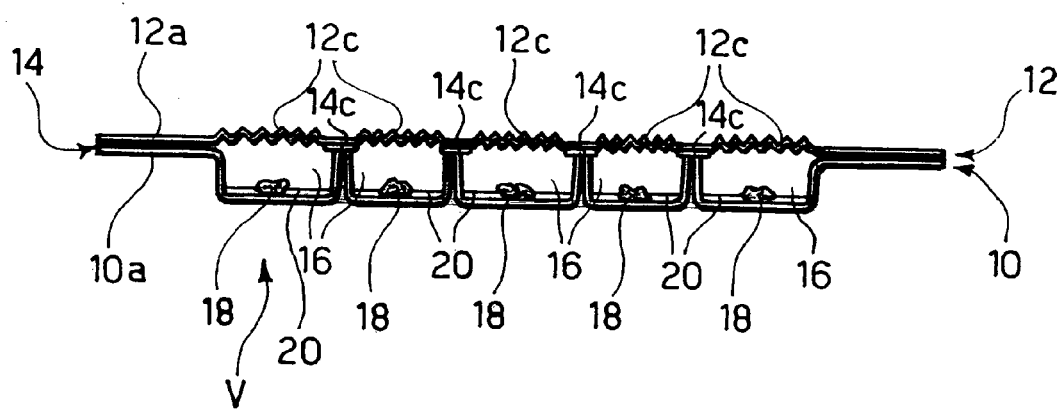
Fig_4

Fig_5
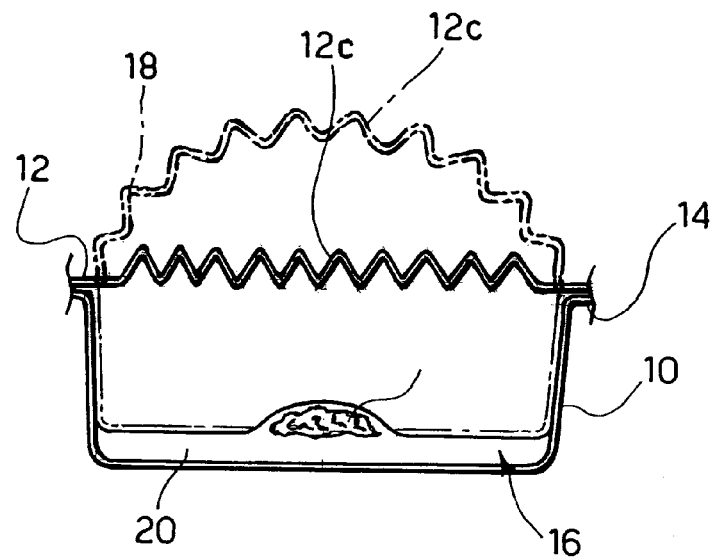
Fig_10
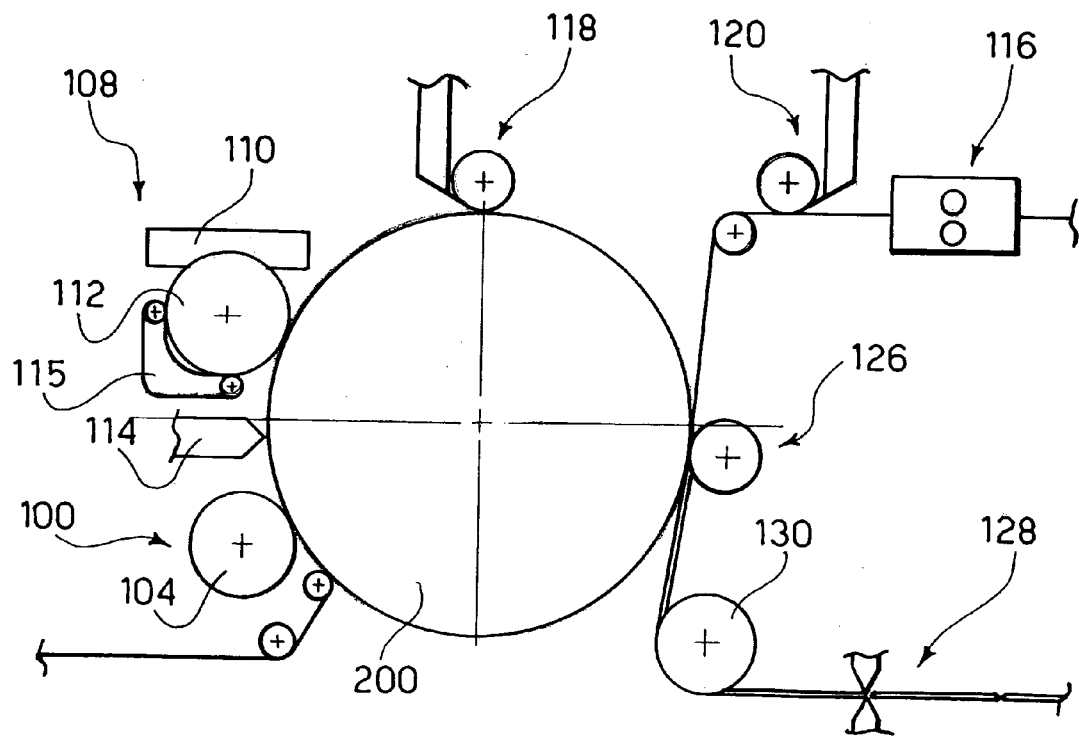

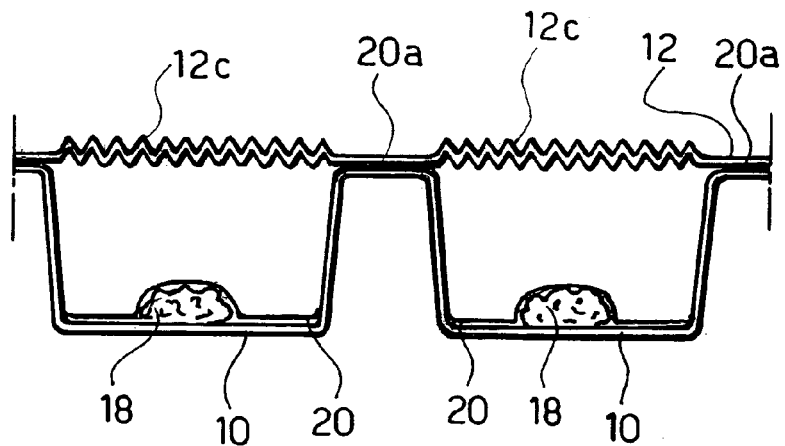
Fig_6
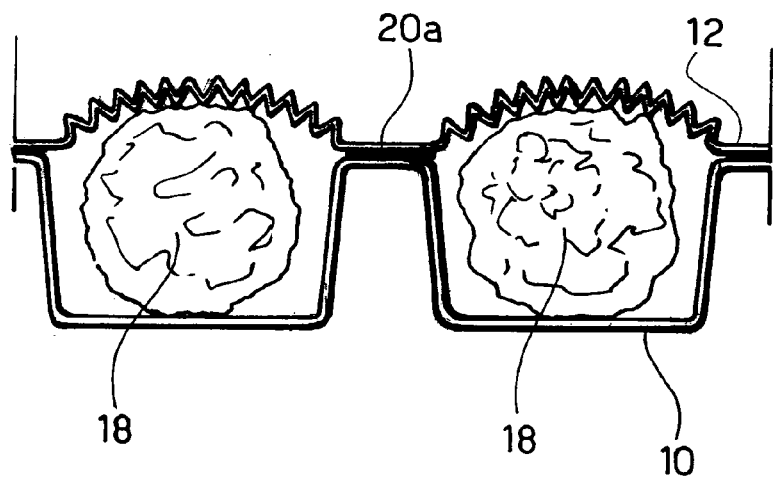
Fig_7
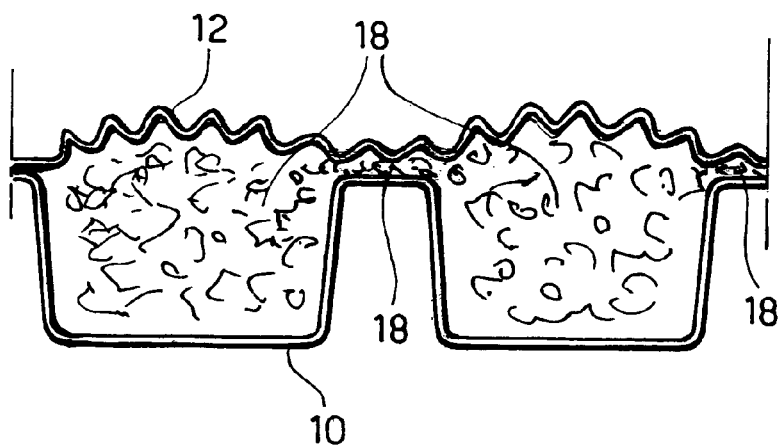
Fig_8

ABSORBING ELEMENT FOR SANITARY PRODUCTS, HAVING EXPANDABLE POCKETS CONTAINING SUPERABSORBENT MATERIAL AND MANUFACTURING PROCESS

This application is the U.S. national phase of International Application No. PCT/IB2007/003904 filed 3 Dec. 2007, which designated the U.S. and claims priority to EP Application No. 07425178.6 filed 26 Mar. 2007, the entire contents of each of which are hereby incorporated by reference.

FIELD OF THE INVENTION

The invention relates to absorbent sanitary articles and specifically regards an absorbent element for an article of this type.

DESCRIPTION OF THE RELATED ART

The term "absorbent sanitary articles" indicates in general articles such as, for example, diapers for babies and small children, sanitary towels for incontinence, pantie-liners for ladies, tampons and the like, designed for absorbing body liquids, being preferentially located in the perineal region of the user.

As schematically illustrated in FIG. 1 of the attached plate of drawings, these articles usually have a stratified structure comprising an outer sheet B impermeable to liquids (commonly referred to as "backsheet"), an inner sheet T permeable to liquids (commonly referred to as "topsheet"), designed to be set in contact with the skin, and an absorbent central insert or core C, which has the function of capturing and storing body liquids. In particular, in the representation of FIG. 1 there is recognizable the typical hourglass configuration of an absorbent sanitary article that can be worn as pants, such as precisely a diaper or a sanitary towel, provided with labels E for closing on the waist.

As is well known to persons skilled in the art, over the course of the years, around this basic structure practically infinite integrations and variants of structure have been developed. These integrations and variants are not, however, of specific importance for the subject treated herein, which is essentially the absorbent core C.

In the first industrially produced diapers appearing on the market at the end of the fifties, the absorbent core C was basically made up of so-called cellulose fluff with different shapes and specific weight (weight per unit surface). Subsequently, the tendency has developed of adding to the cellulose fluff superabsorbent granular materials with a high capacity for retaining liquids.

Said superabsorbent materials are known by different terms, such as, for example, SAP (Super Absorbent Polymer) or AGM (Absorbent Gelling Material).

In the majority of cases, these are hydrogelling materials capable of absorbing and capturing the liquid in a practically stable way.

By way of reference, one gram of cellulose fluff is capable of absorbing 8-10 g of 0.9% saline solution but withholds only an extremely modest fraction thereof, typically 2-3 g.

Instead, one gram of superabsorbent material is capable of absorbing approximately 50 g of saline solution and of withholding approximately 30 g thereof after centrifugation (according to the EDANA 441.1-99 method) or else approximately 22 g under a load of 0.7 psi (according to the EDANA 442.1-99 method).

In view of these characteristics, the idea of creating an absorbent core for sanitary articles, constituted principally, if not exclusively, of superabsorbent material, appears certainly attractive.

In this connection, it should, however, be noted that the fluff has the function both of acquiring and conveying the liquid within the absorbent core. The superabsorbent material has instead, more than anything else, the function of retaining the liquid. For this reason, superabsorbent materials were initially used at low concentrations (70% of fluff, 30% of superabsorbent material). It has in fact been found that concentrations higher than 40% can lead to the phenomenon referred to as "gel-blocking": by swelling, the granules of superabsorbent material create a barrier to the liquids, slowing down the capacity for further acquisition of liquids, until said capacity is practically lost.

This drawback can be overcome at least in part by using superabsorbent materials of a permeable type only recently available on the market. Alternatively, it is possible to intervene on the spatial distribution of fluff/superabsorbent material, or else add to the core materials with characteristics of acquisition and distribution of liquids. These solutions enable the use of concentrations of superabsorbent materials of up to approximately 60 wt % with respect to the core as a whole.

Various patent documents illustrate the possibility of creating an absorbent core without fluff of a traditional type (usually cellulose) by replacing the cellulose fibres with different materials (for example, cellulose acetate). Examples of documents of this kind are the documents US-A-2003/0208174, U.S. Pat. No. 6,068,620, and U.S. Pat. No. 6,832,905. There also exist patent documents that teach how to obtain absorbent cores constituted in a practically exclusive way by superabsorbent material and extracts of materials of various nature. In this connection, documents may be considered, such as U.S. Pat. Nos. 4,578,078, 4,600,458, 4,681,577, 4,685,914, 5,643,238, 5,938,650 or WO-A-2005/004939.

Albeit presenting features of applicational advantage, the solutions, described in said prior documents cannot be considered altogether satisfactory.

In effect, to achieve altogether satisfactory performance, an absorbent core with a base of superabsorbent material should correspond to the ideal model represented in FIG. 2 of the annexed plate of drawings: this consists of a regular lattice of granules 10 of superabsorbent material separated by a "means" X that should be able to:

withhold the granules 10 in the position assigned to them within the lattice, preventing any undesirable displacement thereof when the article is handled and worn;

acquire the body liquid and transfer it completely to the granules 10, enabling the granules 10 themselves to absorb the liquid and undergo swelling;

oppose no resistance to the swelling of the granules 10: rather, the "means" X should in effect disappear as the granules 10 swell in such a way as to cause, once absorption of the liquid is completed, the absorbent core to be constituted exclusively by the swollen granules 10; and continue to acquire liquid during the process of swelling of the granules 10, transferring it through the entire mass of absorbent material, preventing part of this mass from failing to absorb liquid and hence remaining unused.

OBJECT AND SUMMARY OF THE INVENTION

The object of the invention is to provide an absorbent element that approaches the ideal model outlined previously much more closely than occurs for the solutions according to the prior art, to which reference was made previously.

According to the present invention, said object is achieved thanks to an absorbent element for sanitary articles having the characteristics recalled specifically in the ensuing claims. The invention also relates to a corresponding sanitary article and to the method of production of the absorbent element.

The claims form an integral part of the disclosure of the invention provided herein.

BRIEF DESCRIPTION OF THE ANNEXED DRAWINGS

The invention will be described, purely by way of non-limiting example, with reference to the annexed figures of drawing, wherein:

FIGS. 1 and 2 have already been described previously;

FIG. 3 is a perspective view, partially cutaway, of an absorbent element of the type described herein;

FIG. 4 is a cross section according to the line IV-IV of FIG. 3;

FIG. 5 is an enlarged view of the part of FIG. 4 indicated by the arrow V;

FIG. 6 is a cross section according to the line VI-VI of FIG. 3;

FIGS. 7 and 8 are two views substantially homologous to that of FIG. 6, which represent operation of the absorbent element described herein;

FIG. 10 is a schematic illustration of the structure of a device for producing the absorbent element described herein.

DETAILED DESCRIPTION OF EXEMPLARY EMBODIMENTS OF THE INVENTION

Figure 9:
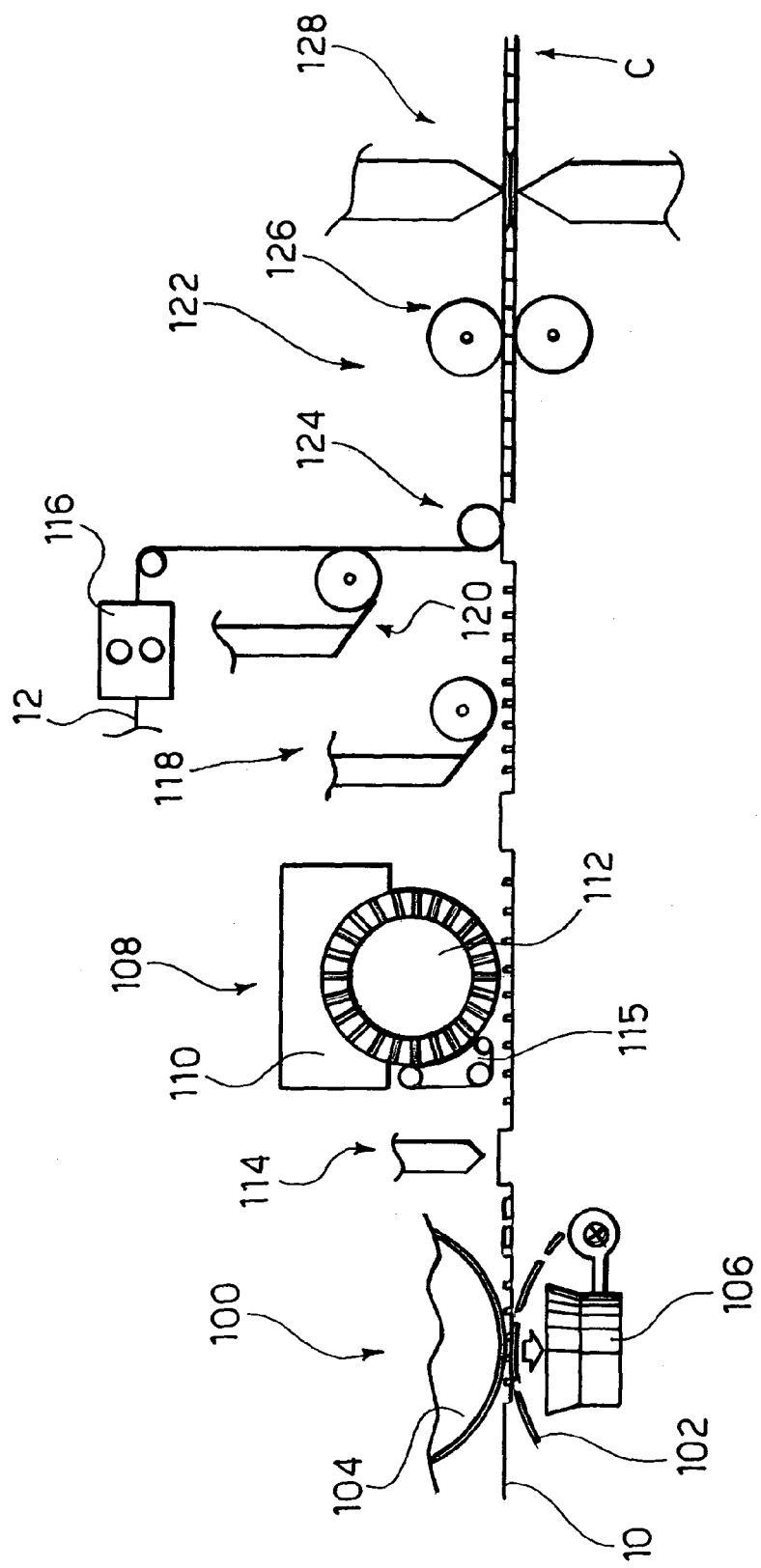
FIG. 9 is a schematic illustration of successive possible steps of a method for the production of the absorbent element described herein.

As in the preceding FIG. 1, in FIG. 3 the reference C designates as a whole an absorbent element that can be used within a sanitary article of the type of the ones referred to in the introductory part of the present description.

In the exemplary embodiments represented herein, the element C basically assumes the form of a flattened body having an overall rectangular shape. This conformation is usable, for example, in the case where the element C is designed to be inserted in a diaper or else in a sanitary towel for incontinence. The rectangular shape is not, however, in any way imperative, in particular for applications in different products, such as, for example, sanitary pantie-liners for ladies, articles in which there is usually preferred, for the absorbent core, a bone shape or an hourglass shape, which is more conformable to the anatomy of the person wearing the article. The ensuing description will on the other hand enable an easier understanding of how the solution described herein is suited to being used according to a wide range of geometries.

As better appreciated from the cross-sectional view of FIG. 4, the absorbent element C has a layered structure comprising two laminar elements or layers of sheet material 10 and 12 connected to one another (according to modalities better described in what follows) by a layer of adhesive 14, constituted for example, by a hot-melt glue, which is widely used in the production of sanitary articles.

At least one, and preferably both of the layers 10 and 12 are permeable to the body fluids that the element C is designed to absorb. In a currently preferred embodiment, the layers of sheet materials 10 and 12 are constituted by non-woven fabric consisting of polypropylene and a mixture of fibres with a specific weight (weight per unit area) in the region of 10 g/m² to 30 g/m².

Materials of this type are widely used in the production of sanitary articles. For reasons of simplicity of description, in what follows reference will be made herein to the layer 10 and to the layer 12 as "bottom" layer and "top" layer, respectively. These terms are used purely by way of reference and are not to be interpreted as in any way limiting the scope of the invention: the absorbent element C is suited in fact to being used according to a practically indifferent orientation.

The intention in saying that—at least one—of the layers 10 and 12 is permeable to the body fluids that are to be absorbed by the absorbent element is to point out the possibility of the other of said layers (for example, the "bottom" layer 10) also being impermeable to body fluids. In this way, the impermeable layer is suited to facing the outside of the absorbent article and to co-operating with the backsheet in the function of retention of body fluids, or else to constituting itself the backsheet.

The bottom layer of sheet material 10 basically presents as an alveolated layer, in the sense that, with the possible exception of two side bands 10a and two head bands 10b (kept preferentially smooth in order to ensure firm connection with homologous bands 12a and 12b of the top sheet 12 for creating a firm lateral grip of the element C), in the layer 10 there are present hollowed or well-like formations 16, obtained according to criteria described more fully in what follows.

In a preferred way, and as may be appreciated better from the perspective view of FIG. 3, the aforesaid hollowed or well-like formations 16 preferentially assume the form of a continuous array of hexagonal cells having (these data have of course a purely orientative value) a depth of approximately 1-10 mm and diametral dimensions in the region of 5-30 mm.

This "honeycomb" conformation constitutes a preferential solution, which optimizes the ratio between the part of area of the layer 10 occupied by the cells 16 and the total area of the layer 10.

This conformation, and in particular the fact that these hollowed formations (in brief, cavities) 16 are hexagonal in shape (set according to an array of cells strictly penetrating one another according to a honeycomb arrangement) is not, however, imperative. The cavities or wells 16 could in fact have any shape (for example, with a circular-mouth profile) and/or be set at a certain distance from one another and/or form an array that, unlike the continuous array illustrated in the annexed plate of drawings, has discontinuities, i.e., areas of the layer 10 where cavities or wells 16 are not present, possibly with the cavities or wells 16 localized only in an area corresponding to the central part of the element C.

Again, whilst in the example illustrated herein the distribution of the cavities or wells 16 is uniform, both as regards the dimensions and as regards the distribution of the cavities or wells 16, non-uniform distributions are certainly included in the scope of the invention, namely, for example, distributions in which:

the cavities or wells 16 have larger dimensions at the centre of the element C and smaller dimensions at the margins of the element C; and/or the density (i.e., the number per unit surface) of the cavities or wells 16 is different at the centre of the element C from at the margins of the element C; for example, with a higher number at the centre than at the margins.

Those of skill in the art will appreciate that non-uniform distributions of this kind are designed to take into account the fact that the discharge of body fluids is localized usually in an area corresponding to an "deposition area" located in the proximity of the centre of the element C, possibly with morphologies that are different according to the sex of the user.

Within the cavities or wells 16 (usually within all of the cavities or wells 16 made in the layer 10), respective amounts 18 of material are present with capacity to absorb body fluids: these are precisely materials known as SAP (Super Absorbent Polymer) or AGM (Absorbent Gelling Material) that are able to withhold, by swelling, large quantities of water and hence of body liquids.

Orientatively (with reference to the cell dimensions indicated previously by way of example), each amount 18 can be constituted for example by 0.05-0.40 g of superabsorbent material. Each of the amounts or masses 18 of superabsorbent material is usually constituted by a certain amount of granules of this material. It is usually preferred that the granules of superabsorbent material should not be deposited freely within the corresponding cavity or well 16 but should be withheld therein by a certain amount of glue 20 designed to bestow a certain coherence upon the amount of superabsorbent material. This is usually a hydrosoluble glue, for example the glue available under the commercial name of Cycloflex, manufactured by the company National Starch (USA). In contact with body liquids, said hydrosoluble glue loses at least in part its characteristics of adhesiveness, so that when the element C starts to absorb liquid, the mass of superabsorbent material 18 detaches from the wall of the cavity or well 16 in which it is located and can thus be freer to expand as a result of the absorption of liquid, co-operating, with the homologous masses 18 that are in the other cavities or wells 16, in the creation of a lattice with anti-collapsing function.

As will be more fully described in what follows, the hydrosoluble glue can also perform the function of keeping the cavities or wells 16 closed as long as the element C remains dry.

In the foregoing description it has at least been implicitly assumed that the masses 18 of superabsorbent material have the same characteristics of absorption and are dosed in a uniform way in the various cavities or wells 16. However, the invention also encompasses the use of masses 18 with differentiated characteristics of absorption (for example, absorption that is faster or more deferred over time) and/or the recourse to non-uniform dosages in the various cavities or wells 16 (i.e., causing the masses 18 of superabsorbent material to be distributed in different amounts in different areas of the element), the foregoing having the purpose of modulating in time and/or in space the qualities of absorption of the various areas of the element C.

Joint observation of FIGS. 3 and 4 will highlight the morphology of the layer of glue 14 that connects the layers 10 and 12. This layer comprises:

two side strips 14a that connect to one another the layers 10 and 12 in areas corresponding to the side bands 10a and 12a; and two head strips 14b that connect to one another the layers 10 and 12 in areas corresponding to the head bands 10b and 12b.

In addition to the aforesaid side strips and head strips, designed to create an external line of sealing between the two layers of sheets 10 and 12 extending along the border of the element C, the layer of glue 14 also comprises a plurality of strips 14c, which extend, set apart from one another (for example, by a distance comprised between a minimum of 1 mm and a maximum of 30 mm) for connection of the layers 10 and 12 in the area where the cavities or wells 16 are located.

The glue of the layer 14 is a stable, non-hydrosoluble, glue, such as typically a glue of a hot-melt type. The fact that the strips 14c (illustrated herein as continuous, but which may consist also of discrete stretches) are set apart from one another is aimed at preventing the mouth parts of the cavities or wells 16—on which the layer 12 extends to provide a covering—from being undesirably occluded by the glue. For example, with the values of distance between the strips 14c indicated above, it is possible to proceed in such a way that, according to the shape and the dimensions of the mouth part of the cavities or wells 16, the mouth surface of said cavities or wells 16 is kept free from the glue 14c for a fraction that ranges from one third of the surface to the entire surface (i.e., from 33% to 100%) of said surface.

The configuration illustrated herein, with the presence of strips of glue 14c oriented in the direction of principal extension of the element C, constitutes just one from among the various possible solutions that enable the desired effect to be achieved (distributed connection of the layers 10 and 12, without producing the complete occlusion of the mouth parts of the cavities or wells 16).

The same result could be obtained, for example, using strips of glue that extend not "lengthwise", as in the case of the strips 14c that may be seen in FIG. 3, but in a direction exactly orthogonal (hence "crosswise") with respect to the element C.

Other alternative solutions can envisage strips of glue extending in a direction inclined with respect to the element C or else according to a zigzag path, or else continuous or discontinuous formations of glue applied according to different geometrical configurations, such as for example diamond shapes or paths that reproduce at least locally the paths of the mouth parts of the cavities or wells 16.

Again, the surface of distribution of the glue of the layer 14 (whatever the shape) can be non-uniform on the surface of development of the element C so as to bestow upon the element C characteristics of flexibility and/or deformability differentiated from area to area in order to improve the qualities of anatomical adherence to the body of the user.

The configuration illustrated herein by way of example (strips of glue 14c oriented in the direction of principal extension of the element C) is currently preferred for at least two reasons:

it allows (or, at least, does not appreciably hinder) the possibility of the element C to bend in a transverse direction according to a general channel-like configuration: this configuration facilitates the collection and containment of the fluids, proving likewise more effective from the standpoint of the anatomical comformability of the element C and of the article that comprises it;

it induces setting-up, in the area of transition or interface between the layers 10 and 12, of channels of diffusion of the liquid from the centre (depot area) towards the ends of the element C.

In addition to presenting the side bands 12a and head bands 12b kept preferentially smooth (to facilitate the adhesive connection with the side bands 10a and head bands 10b of the layer 10), the layer 12 is a layer with characteristics of compliance.

These characteristics can be intrinsic ones of the sheet material constituting the layer 12.

Usually, these characteristics are, however, obtained by subjecting said material to a process such as to bestow thereon, or else enhance, said characteristics.

In a possible embodiment, this result is obtained by subjecting the central portion of the top sheet 12—hence with the exclusion of the bands 12a and 12b—to an operation of "activation" i.e., of weakening such as to weaken/break the connections between the fibres of the non-woven fabric of the layer 12 in a transverse direction with respect to the element C (i.e., in a transverse direction with respect to the lines of glue 14c).

The term "activation" recalls the fact that such a treatment is commonly carried out in elasticized non-woven materials in order to make them "active", i.e., more easily extendible elastically.

Further modalities of treatment, such as to enable, in an area corresponding to the aforesaid central part, the sheet 12 to present characteristics of compliance, are substantially within the reach of the person skilled in the art: for example, the material of the layer 12 could be subjected to a treatment of (micro)pleating in a transverse and/or longitudinal direction with respect to the element C.

The general pleated pattern of the portions 12c that may be seen in FIGS. 4 to 8 of the annexed plate of drawings must then be interpreted as a figurative representation of the characteristic of compliance, without specific reference to the modalities with which said characteristic is obtained.

Whatever the specific solution adopted, in an area corresponding to the portions 12c, where the layer 12 is not connected adhesively to the bottom layer 10 by the strips of glue 14c, the layer 12 can deform in a direction opposite with respect to the mouth parts of the cavities or wells 16.

Albeit without wishing to attribute a binding character to this quantitative datum, the degree of compliance recommended for the portions 12c is such that, yielding under the thrust of the masses 18, the portions 12c are subjected to a linear extension in a ratio from approximately 1.5:1 to approximately 3:1 with respect to the initial value; i.e., yielding under the thrust of the masses 18, the portions 12c are able to lengthen up to twice or three times with respect to the adjacent areas of the layer 12.

This capacity for deformation of the top layer 12 is designed to enable the layer 12 to deform when, as a result of the gradual absorption of the body liquids, after occupying the respective cavities 16 entirely, the masses of superabsorbent material 18 tend to expand (as schematically illustrated with a dashed line in FIG. 5) beyond the mouth edges of the cavities 16 themselves.

The striplike distribution 14c (or, in general, discontinuous distribution) of the glue 14 is precisely designed to enable free expansion of the aforesaid masses of superabsorbent material 18. By swelling as a result of the absorption of the liquid that penetrates into the element C through at least one or preferably both of the layers 10 and 12, after completely or practically completely occupying the respective cavity or well 16, the masses 18 are hence free to press against the layer 12, without finding in the glue 14 an appreciable obstacle to the further deformation.

The masses of superabsorbent material 18 press against the layer 12, which, owing to the presence in the compliant regions 12c, yields under the thrust of the masses 18. The phenomenon of expansion of the superabsorbent masses 18 (and hence the absorption of fluid) can thus take the form of:
 a "first level", corresponding to the filling of the respective cavity or well 16; and
 a "second level", represented by the further step of expansion of the masses 18 beyond the mouth edge of the respective cavity or well 16.

As already mentioned previously, the use of hydrosoluble glue can be extended to the function of keeping the cavities or wells 16 closed as long as the element C remains dry. In particular (usually concomitantly with the application of the glue 20 that withholds the masses of superabsorbent material 18), further formations 20a of hydrosoluble glue can be applied on the "bridges" that separate adjacent cavities or wells 16 in the longitudinal direction of the element C: see in this connection, FIG. 3.

As may be appreciated better from the cross-sectional view of FIG. 6, as long as the element C is dry (i.e., before absorption of body fluids starts), the portion of layer 12 set covering each cavity or well 16 in effect closes said cavity or well 16, which—like the mass of superabsorbent material 18 contained therein—is hence:
 separated from the adjacent cavities or wells 16 in the direction transverse to the element C by the strips of (permanent) glue 14c; and
 separated from the adjacent cavities or wells 16 in the longitudinal direction of the element C by the formations of (hydrosoluble and hence non-permanent) glue 20a.

When the element C starts to absorb fluid, the formations of hydrosoluble glue 20a lose their adhesive power. The layer 12 then tends to detach from the layer 10, where before the two layers 10 and 12 were connected together by the glue 20a (see FIG. 7). This detachment occurs under the thrust of the superabsorbent material 18, which expands. In this way, at the "second level" of expansion, the superabsorbent masses 18 (which, at the "first level" of expansion, are confined in their cavities 16) can instead overflow into the adjacent cavities 16 in the longitudinal direction of the element C, and this also to quite a considerable extent, as will be better appreciated from FIG. 8.

By way of orientative example, the aforesaid mechanism of two-level expansion enables the masses of superabsorbent material to expand in a ratio such that, setting the total volumetric expansion of the superabsorbent material ideally at 100, approximately 70-90% of the expansion is obtained at the "first level" (i.e., within the cavities or wells 16), whilst the remaining 30-10% is obtained at the "second level" of expansion, after failure of the bond established by the formations of glue 20a.

It will be appreciated in this connection, that:
 above all in the case where the cavities or wells 16 are obtained according to a dense honeycomb network of hexagonal cells, when the masses of superabsorbent material 18 are completely expanded, the volume of the element C is constituted in a practically integral way (except for the side bands and the head bands) by superabsorbent material that has absorbed body liquids;
 also when the process of absorption of the liquid occurs at the second level, the masses 18 continue to be anchored in the respective cavities or wells 16; hence, they do not collapse against one another (for example, accumulating by gravity in an undesirable way at the centre of the crotch element C) and maintain a high exposure to the liquid arriving, minimizing the onset of phenomena of gel blocking.

FIG. 9 is a schematic illustration of the sequence of execution of the various operations that lead to creating the absorbent element C described previously.

In particular, the reference 100 designates the workstation in which, starting from a sheet of smooth material (for example, non-woven fabric with a substance of approximately 10-30 g/m$^2$) formation of the cavities or wells 16 is carried out. For this purpose, it is envisaged that the sheet will be made to pass over a forming mould, basically constituted by a mesh 102 provided with apertures having a profile (for example, hexagonal) that reproduces the mouth edges of the cavities or wells 16.

The sheet material 10 is pressed against the aforesaid forming mesh 102 by an impression roller 104 provided with punches, which force the material 10 into the cavities of the mesh 102 to form the cavities or wells 16. The process of forming can be facilitated by the presence, on the side of the mesh 102 opposite to the material 10 and to the roller 104, of a level of subatmospheric pressure produced by a suction source 106.

The depth of the cavities 16 present in the mould 102 (for example, 10 mm) enables creation of a correct shaping of the cavities or wells 16, preventing any undesirable tearing or perforation of the sheet material 10 (which can present non-isotropic characteristics of tensile strength in a longitudinal direction and in a transverse direction), in particular when a polygonal profile, for example a hexagonal profile, is bestowed upon the cavity 16.

The alveolated layer 10 thus formed advances then towards a station 114, in which into the cavities or wells 16 are poured, in a way in itself known, the masses of hydrosoluble glue 20. The same station 114 can also provide, once again in a known way, for depositing of the glue formations 20a.

Once again with reference to FIG. 9, the reference 108 designates a workstation where the masses of superabsorbent material 18 are metered within the cavities 16. In a preferred way, the dosing station 108 comprises a container or tank 110 that contains the powdered superabsorbent material and functions as vibration doser co-operating with a dosing "wheel" 112. This is basically a drum, the outer surface of which is provided with dosing holes distributed according to a geometrical pattern similar to the geometrical distribution of the cavities or wells 16 made in the sheet material 10.

Loading of the powdered superabsorbent material on the dosing roller 112 and delivery of the material into the cavities or wells 16 occur preferentially using a pneumatic mechanism.

In particular, the path of rotation of the outer surface of the dosing roller 112 envisages that, in a region of loading, where the holes of the dosing roller 112 currently facing towards the container 110 are located, the holes of the dosing roller 112 are brought to a level of subatmospheric pressure and are filled with superabsorbent material sucked in from the container 110.

The condition of subatmospheric pressure is maintained in the holes in order to prevent, with the possible aid of a containment strip 115, the superabsorbent material from coming out of the holes of the dosing roller.

When, as a result of the movement of rotation of the roller 112, the holes previously charged with superabsorbent material are set facing downwards, towards the sheet material 10, a jet of air coming from within the roller 112 expels, from the holes, the powdered superabsorbent material, which is thus deposited in the cavities or wells 16 of the sheet material 10.

Again as a result of the rotation of the roller 112, once the superabsorbent material contained in the holes has been expelled, the holes return towards the top to reach again the position in which they face the container or tank 110. During said movement of return towards the container 110, the holes undergo cleaning with a flow of ionized and heated air in order to prevent any contamination.

Usually associated to the metering roller 112 are sealing elements acting both in the axial direction and in the tangential direction in order to prevent the powdered superabsorbent material from being dispersed and being drawn beyond the area of depositing in the cavities or wells 16. The axial sealing elements can be constituted by pressurized slots provided on the vertical shoulders of the overlying container 110, with the possible addition of suction holes that capture any granules that may have leaked out. In the tangential direction, the seal is constituted preferentially by scraping elements that function substantially as doctor blades in regard to the outer surface of the dosing roller. These scraping elements can have associated to them jets of air and suction cavities for collecting any grains of powder of superabsorbent material that may have leaked out.

The reference number 116 designates the workstation that carries out the so-called operation of "activation" of the topsheet material 12, designed to cause the top layer 12 to be compliant under the thrust exerted by the masses of superabsorbent material 18 so as to enable expansion of the masses 18 at the "second level".

In a known way, the station 116 comprises two counter-rotating rollers with complementary circumferential grooves that grip between them the material of the layer 12 and engage one another with an interval or gap that can be adjusted with precision so as to create the desired action of "activation". At least one of the aforesaid rollers has smooth end bands and discontinuities in the grooves such as to cause activation of the layer 12 not to occur in areas corresponding to the side bands 12a and head bands 12b (FIG. 3), where it is desired that the material of the layer 12 should conserve its initial toughness. The station 116 usually also applies a longitudinal tensile force on the sheet material 12.

The references 118 and 120 designate two stations for application of glue (for example, of a hot-melt kind) of a known type, designed to deposit the formations of glue 14a, 14b and 14c on the layers 10 and 12.

The presence of two workstations designed to operate distinctly on the two layers of sheet material and 12 is not in itself imperative. The glue 14 could be applied also on just one of said layers of sheet material with a view to their subsequent coupling together. FIGS. 9 and 10 refer to a preferential embodiment, where it is envisaged that the station 118 applies the external side strips 114a and head strips 14b on the bottom layer 10, whilst the unit 120 applies the strips 14c on the sheet material of the layer 12.

Of course, the modes of application of the glue can be modified according to the needs, in particular when the overall geometry of the element C changes. This applies also to the hydrosoluble glue: for example, the formations 20a could be applied (instead of in the station 114, as hypothesised herein) concomitantly with the strips 14c.

After receiving the layer or layers of glue 14, the two layers 10 and 12 are superimposed on one another, causing them to pass into a pressing station 126 (for example a roller pressing station), which presses the layers 10 or 12 against one another in an areas corresponding to the strips of glue 14a, 14b and 14c, which, solidifying, connect the two layers 10 and 12 together, bestowing final coherence on the element C.

The semifinished product thus obtained is then made to advance towards a segmentation station 128, which segments the chain of elements C so far connected to one another, acting in the end areas 10b and 12b connected to one another by the strips of glue 14b, thus giving rise to individual elements C.

The view of FIG. 10 (where devices and components that are identical or equivalent to the ones already described in relation to FIG. 9 are designated by the same reference numbers) highlights how—according to a particularly preferred embodiment—a fair part of the treatment stations described previously are preferably distributed around a carousel structure 200 substantially resembling a wheel or roller, the outer surface of which defines a winding path first for the sheet constituting the layer 10, then for the layer 12, which is applied against the shaped layer 10 to form the cavities or wells 16 and is filled with the masses of superabsorbent material 18, and finally for the semifinished product resulting from the coupling of the layers 10 and 12.

Advantageously, the wheel or roller constituting the carousel structure 200 has an outer surface perforated in a way complementary to the cavities or wells 16 and is provided with one or more internal cavities that can be brought to a different level of pressure according to the stretch of winding path considered.

In this way, the outer surface of the carousel structure 200 is able to perform the function of the perforated mould for the formation of cavities or wells 16 (mould 102 of FIG. 9) and, in general, to ensure a firm retention of the layer 10 (subsequently coupled to the layer 12), this in so far as the cavities or wells 16 continue to be received in the holes of the outer surface of the carousel structure 200 until the final composite product (obtained in the station 126, substantially constituted by a roller that presses the layer of sheet material 12 against the layer of sheet material 10 with interposition of the layer of glue 14) is separated, as represented by the reference number 130, from the surface of the carousel structure 200 by extracting the cavities or wells 16 from the holes of the outer surface of the structure 200 itself.

Of course, without prejudice to the principle of the invention, the details of construction and the embodiments may vary, even to a marked extent, with respect to what is illustrated herein purely by way of non-limiting example, without thereby departing from the scope of the invention, as defined by the annexed claims. This applies in particular, but not exclusively, to the possibility of replicating the solution described herein so as to give rise to a multiple absorbent element C constituted by the superposition of a number of elements of the type described and illustrated herein, possibly comprising superabsorbent materials with differentiated characteristics of absorption (for example, an absorption that is faster or more deferred over time). Such a multiple element can be simply constituted by a layer 10 of the type described herein, the alveolated structure of which is used, exploiting the cavities present on both faces of the layer 10 for charging with superabsorbent material (if necessary, with differentiated characteristics of absorption on the opposite faces), and by two layers 12—once again of the type described herein—applied for covering the cavities on the two opposite faces of the layer 10.

The invention claimed is:

1. An absorbent element for the absorption of body fluids in sanitary articles, comprising:
   a first layer of sheet material presenting an array of hollowed formations with respective mouth parts;
   masses of superabsorbent material arranged in the hollowed formations and expandable as a result of the absorption of body fluid; and
   a second layer of sheet material, applied on said first layer of sheet material covering the mouth parts of said hollowed formations, wherein
   at least one of said first and second layers of sheet material is permeable to body fluids to enable the body fluids themselves to penetrate into said hollowed formations and be absorbed by said masses of superabsorbent material that expand in said hollowed formations;
   said second layer of sheet material is compliant in an area corresponding to the mouth parts of said hollowed formations, enabling the further expansion of said masses of superabsorbent material beyond said hollowed formations; and
   said first and second layers of sheet material are connected to one another by adhesive formations that extend in an area where said hollowed formations are located, said adhesive formations leaving at least partially free the mouth parts of said hollowed formations, and wherein
   said adhesive formations include both stable adhesive formations that leave the mouth parts of said hollowed formations at least partially free and hydrosoluble adhesive formations that connect said first and second layers of sheet material so as to separate hollowed formations set adjacent to one another, said hydrosoluble adhesive formations being soluble by said body fluids to enable said further expansion of said masses of superabsorbent material beyond said hollowed formations.

2. The element according to claim 1, wherein said adhesive formations leave the mouth parts of said hollowed formations free for a fraction that ranges from 33% to 100% of the area of said mouth parts.

3. The element according to claim 1, wherein both of said layers of sheet material are permeable to said body fluids.

4. The element according to claim 1, wherein said first layer of sheet material is exempt from said hollowed formations in an area corresponding to at least part of its border.

5. The element according to claim 1, wherein said hollowed formations form a continuous array in said first layer of sheet material.

6. The element according to claim 1, wherein said hollowed formations define a uniform array.

7. The element according to claim 1, wherein said hollowed formations are hexagonal in shape, so that said array has a honeycomb appearance.

8. The element according to claim 1, wherein at least one of said first layer and said second layer of sheet material is made of non-woven fabric.

9. The element according to claim 1, wherein at least in an area corresponding to the mouth parts of said hollowed formations of said first layer of sheet material, said second layer of sheet material present areas that are more compliant than the adjacent areas of said second layer of sheet material.

10. The element according to claim 9, wherein said areas of greater compliance are weakened or pleated areas.

11. The element according to claim 9, wherein said areas of greater compliance have a capacity of extension increased by 1.5 to 3 times with respect to the adjacent areas of said second layer of sheet material.

12. The element according to claim 9, wherein said second layer of sheet material is exempt from said areas of greater compliance in an area corresponding to at least part of its border.

13. The element according to claim 1, wherein at least in areas corresponding to said hollowed formations, said adhesive formations are in the form of strips.

14. The element according to claim 13, wherein said strips of adhesive formations extend in a longitudinal direction with respect to the element.

15. The element according to claim 13, wherein said strips of adhesive formations are set apart from one another by gaps.

16. The element according to claim 15, wherein said gaps have a width of between 1 and 30 mm.

17. The element according to claim 1, wherein said adhesive formations consist of hot-melt glue.

18. The element according to claim 1, wherein said masses of superabsorbent material are anchored in said hollowed formations by a hydrosoluble adhesive soluble by said body fluids.

19. The element according to claim 1, wherein said masses of superabsorbent material are distributed in different amounts in different areas of the element.

20. The element according to claim 1, wherein, following absorption of body fluids, said masses of superabsorbent material expand:
for 70-90% of their overall volume of expansion, in said hollowed formations; and
for the remaining 30-10% of their overall volume of expansion beyond said hollowed formations.

21. The element according to claim 1, comprising:
a said first layer of sheet material presenting arrays of hollowed formations with respective mouth parts on both of its two opposite faces, said hollowed formations receiving masses of superabsorbent material that is able to expand as a result of the absorption of body fluid; and
a pair of said second layers of sheet material applied on the opposite faces of said first layer of sheet material so as to cover the mouth parts of said hollowed formations.

22. The element according to claim 21, wherein said hollowed formations receive masses of superabsorbent material with characteristics of absorption of body fluid differentiated between the two opposite faces of said first layer of sheet material.

23. A sanitary article comprising an absorbent element according to claim 1.

24. A sanitary article comprising a plurality of absorbent elements according to claim 1.

25. The sanitary article according to claim 24, wherein the absorbent elements of said plurality have characteristics of absorption differentiated from one another.

26. A method for producing absorbent elements for the absorption of body fluids in sanitary articles, comprising the operations of:
(a) providing a first layer of sheet material presenting an array of hollowed formations with respective mouth parts;
(b) arranging in said hollowed formations masses of superabsorbent material expandable as a result of the absorption of body fluid;
(c) applying a second layer of sheet material covering the mouth parts of said hollowed formations of said first layer of sheet material;
(d) using, for at least one of said first and second layers, a layer of sheet material permeable to body fluids to enable the body fluids themselves to penetrate into said hollowed formations and be absorbed by said masses of superabsorbent material that expand in said hollowed formations, said second layer of sheet material being compliant in an area corresponding to the mouth parts of said hollowed formations, wherein said second layer of sheet material can deform in a direction opposite with respect to the mouth parts of said hollowed formations thus enabling the further expansion of said masses of superabsorbent material beyond said hollowed formations, and
(e) connecting to one another said first and second layers of sheet material with adhesive formations that extend in the area where said hollowed formations are located and leave the mouth parts of said hollowed formations at least partially free, wherein
said connecting operation includes connecting to one another the said first layer and said second layer of sheet material both with stable adhesive formations which leave the mouth parts of said hollowed formations at least partially free, and with hydrosoluble adhesive formations set so as to separate hollowed formations adjacent to one another, the hydrosoluble adhesive formations being soluble by said body fluids to enable said further expansion of said masses of superabsorbent material beyond said hollowed formations.

27. The method according to claim 26, comprising the operation of leaving the mouth parts of said hollowed formations free for a fraction that ranges from 33% to 100% of an area of said mouth parts.

28. The method according to claim 26, comprising the operation of using for both of said layers of sheet material materials permeable to said body fluids.

29. The method according to claim 26, comprising the operation of leaving said first layer of sheet material exempt from said hollowed formations in an area corresponding to at least part of its border.

30. The method according to claim 26, wherein said hollowed formations form a continuous array in said first layer of sheet material.

31. The method according to claim 26, wherein said hollowed formations define a uniform array.

32. The method according to claim 26, wherein said hollowed formations are hexagonal in shape, so that said array has a honeycomb appearance.

33. The method according to claim 26, comprising the operation of using non-woven fabric for at least one of said first layer and said second layer of sheet material.

34. The method according to claim 26, comprising the operation of providing, in said second layer of sheet material, at least in an area corresponding to the mouth parts of said hollowed formations of said first layer of sheet material, areas that are more compliant than the adjacent areas of said second layer of sheet material.

35. The method according to claim 34, comprising the operation of forming said areas of greater compliance via weakening or pleating.

36. The method according to claim 34, comprising the operation of forming said areas of greater compliance with capacity of extension increased by 1.5 to 3 times with respect to adjacent areas of said second layer of sheet material.

37. The method according to claim 34, comprising the operation of leaving said second layer of sheet material without said areas of greater compliance in an area corresponding to at least part of its border.

38. The method according to claim 26, comprising the operation of creating said adhesive formations in the form of strips at least in an area corresponding to said hollowed formations.

39. The method according to claim 38, comprising the operation of creating said adhesive formations, at least in an area corresponding to said hollowed formations, in the form of strips that extend in a longitudinal direction with respect to the element.

40. The method according to claim 38, comprising the operation of creating said adhesive formations, at least in an area corresponding to said hollowed formations, in the form of strips set apart from one another by gaps.

41. The method according to claim 40, in which said gaps have a width of between 1 and 30 mm.

42. The method according to claim 26, in which said adhesive formations consist of hot-melt glue.

43. The method according to claim 26, comprising the operation of anchoring said masses of superabsorbent material in said hollowed formations with a hydrosoluble adhesive soluble by said body fluids.

44. The method according to claim 26, comprising the operation of distributing said masses of superabsorbent material in different amounts in different areas of the element.

45. The method according to claim 26, in which, following the absorption of body fluids, said masses of superabsorbent material expand:
- for 70-90% of their overall volume of expansion, in said hollowed formations,
- for the remaining 30-10% of their overall volume of expansion, beyond said hollowed formations.

46. The method according to claim 26, comprising the operations of:
- providing a said first layer of sheet material presenting arrays of hollowed formations with respective mouth parts on both of its two opposite faces;
- arranging in said hollowed formations masses of superabsorbent material that is able to expand as a result of the absorption of body fluid; and
- applying a pair of said second layers of sheet material on the opposite faces of said first layer of sheet material so as to cover the mouth parts of said hollowed formations.

47. The method according to claim 46, comprising the operation of arranging, in said hollowed formations, superabsorbent material with characteristics of absorption of body fluid differentiated between the two opposite faces of said first layer of sheet material.

48. The method according to claim 26, in which at least the operations of providing an array of hollowed formations with respective mouth parts in said first layer of sheet material, arranging said masses of superabsorbent material in said hollowed formations, and applying said second layer of sheet material on said first layer of sheet material are performed in workstations set around a carousel structure for drawing of said first layer of sheet material.

\* \* \* \* \*